United States Patent
Kann (10) Patent No.: US 10,226,230 B2
(45) Date of Patent: Mar. 12, 2019

(54) ULTRASOUND IMAGING SYSTEM IMAGE IDENTIFICATION AND DISPLAY

(71) Applicant: B-K MEDICAL APS, Herlev (DK)

(72) Inventor: Peter Ulrik Kann, Farum (DK)

(73) Assignee: B-K Medical Aps, Herlev (DK)

( * ) Notice: Subject to any disclaimer, the term of this patent is extended or adjusted under 35 U.S.C. 154(b) by 1340 days.

(21) Appl. No.: 13/913,580

(22) Filed: Jun. 10, 2013

(65) Prior Publication Data

US 2014/0364731 A1  Dec. 11, 2014

(51) Int. Cl.
 *A61B 8/00* (2006.01)
 *G06F 1/00* (2006.01)
 *A61B 8/08* (2006.01)

(52) U.S. Cl.
 CPC ............ *A61B 8/463* (2013.01); *A61B 8/4455* (2013.01); *A61B 8/461* (2013.01); *A61B 8/467* (2013.01); *A61B 8/54* (2013.01); *A61B 8/4472* (2013.01); *A61B 8/4483* (2013.01); *A61B 8/469* (2013.01); *A61B 8/5207* (2013.01)

(58) Field of Classification Search
 CPC ......... A61B 8/463; A61B 8/4472; A61B 8/54; A61B 8/5407; A61B 8/4483; A61B 8/469; A61B 8/461; A61B 8/467; A61B 6/461; A61B 6/467; A61B 6/469; A61B 1/00039
 USPC .................................................. 715/718, 863
 See application file for complete search history.

(56) References Cited

U.S. PATENT DOCUMENTS

| | | | | |
|---|---|---|---|---|
| 6,516,215 | B1* | 2/2003 | Roundhill | A61B 8/00 600/432 |
| 2004/0267122 | A1* | 12/2004 | Nadadur | A61B 8/08 600/440 |
| 2009/0021475 | A1* | 1/2009 | Steinle | G06F 19/3406 345/156 |
| 2011/0113329 | A1* | 5/2011 | Pusateri | G06F 3/04883 715/702 |

OTHER PUBLICATIONS

PanasonicUK, "Panasonic Smart VIERA—Swipe and Share", Internet, uploaded Apr. 11, 2013; retrieved from the Internet Dec. 9, 2015 at https://www.youtube.com/watch?v=4Sbny3tXJY8.*

* cited by examiner

*Primary Examiner* — Amanda Lauritzen Moher
*Assistant Examiner* — Katherine McDonald
(74) *Attorney, Agent, or Firm* — Anthony M. Del Zoppo, III; Daugherty & Del Zoppo Co., LPA (57) ABSTRACT

An ultrasound imaging system includes at least one transducer element. The ultrasound imaging system further includes a console with a transducer controller that controls the at least one element, a transducer processor that processes information detected by the at least one element, and a display controller that controls display of the processed information. The ultrasound imaging system further includes a display monitor with a first image display region. The ultrasound imaging system further includes a touch screen keyboard with a second image display region, wherein the display monitor and the touch screen keyboard are separate devices.

25 Claims, 6 Drawing Sheets

ULTRASOUND IMAGING SYSTEM IMAGE IDENTIFICATION AND DISPLAY

TECHNICAL FIELD

The following generally relates to ultrasound and more particular to identification of one or more images to display and the display of the identified one or more images, and is described with particular application to an ultrasound imaging system.

BACKGROUND

An ultrasound imaging system has included an ultrasound probe with a transducer, a console with an internal or external display monitor, and a keyboard. The transducer transmits an ultrasound signal into a field of view and receives echoes produced in response to the signal interacting with structure therein. The echoes are conveyed to the console via a cable or the like and are processed, producing images of the scanned structure, which may be visually presented in a display region of the display monitor.

The display monitor has included a cathode ray tube (CRT), a liquid crystal display (LCD), light emitting diode (LED), and/or other monitor. Furthermore, the display monitor has been a monitor with no processor or processing capabilities and that is simply an output device that accepts and displays data from a processor of the console. With such display monitors, generally, the display monitor faces the clinician operating the ultrasound imaging system. In this manner, the clinician can visually observe rendered images and readily access controls for invoking visualization and non-visualization features.

To show a patient and/or other person a rendered image, the clinician would have to turn the display monitor so that the display region is in the line of sight of the patient and/or the other person. Unfortunately, this may make it difficult for the clinician to concurrently observe the rendered image. Furthermore, with an integrated console/monitor, the clinician may have to turn the console and thus may no longer have easy access to the visualization and non-visualization controls of the console. Moreover, displayed text, graphics, etc. also displayed may clutter the display region and limit the size of the rendered image.

SUMMARY

Aspects of the application address the above matters, and others.

In one aspect, an ultrasound imaging system includes at least one transducer element. The ultrasound imaging system further includes a console with a transducer controller that controls the at least one element, a transducer processor that processes information detected by the at least one element, and a display controller that controls display of the processed information. The ultrasound imaging system further includes a display monitor with a first image display region. The ultrasound imaging system further includes a touch screen keyboard with a second image display region, wherein the display monitor and the touch screen keyboard are separate devices.

In another aspect, a method includes receiving a first signal from a touch screen keyboard of an ultrasound imaging system indicating one of a plurality of images to display with a display monitor of the ultrasound imaging system, wherein the touch screen keyboard and the display monitor are separate devices, and displaying the one of the plurality of images with the display monitor.

In another aspect, a computer readable storage medium is encoded with computer readable instructions which, when executed by a computer processor, cause the computer process to: display, in an image display region of a display monitor of an ultrasound imaging system, an image from a set of images displayed in an image display region of a touch screen keyboard based on a signal from the touch screen keyboard indicative of an imaged of interest, wherein the touch screen keyboard and the display monitor are separate devices.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
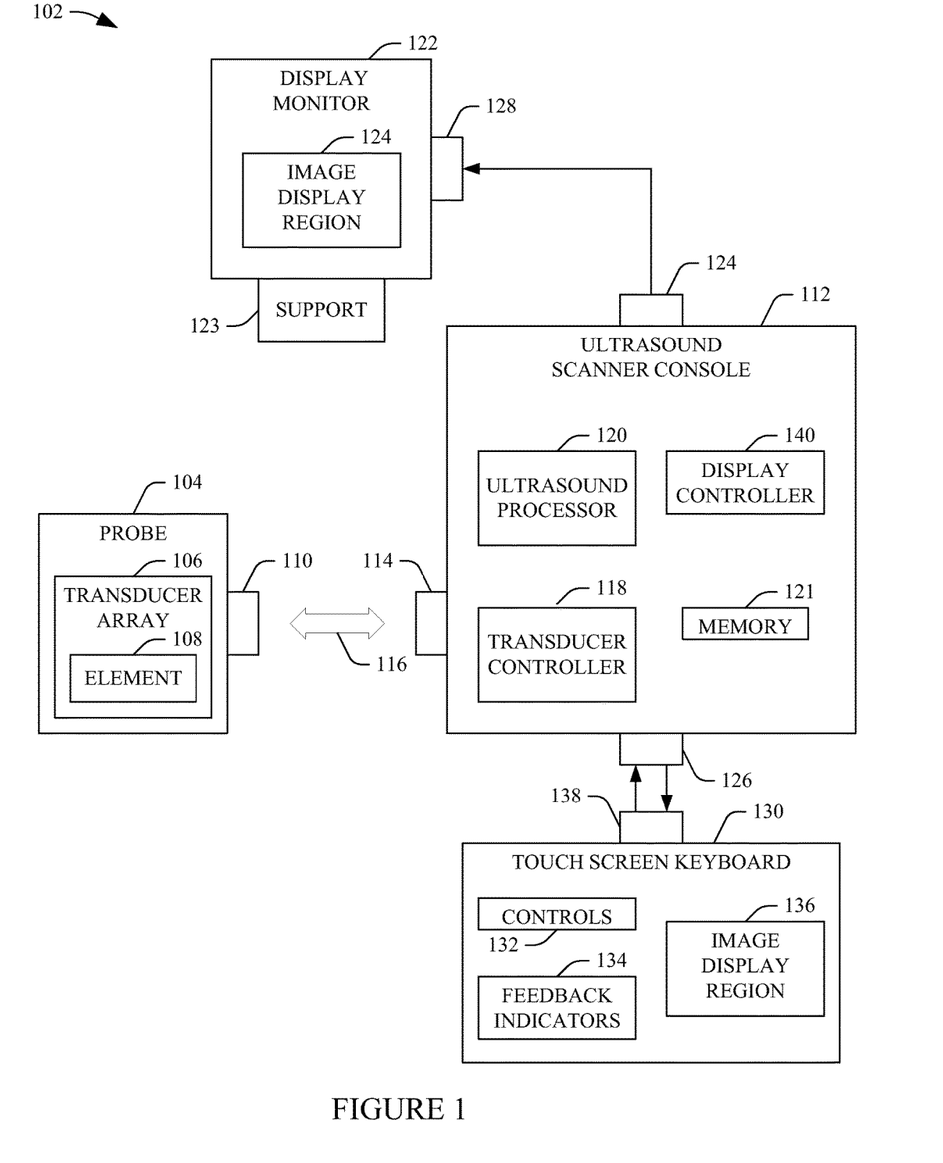
FIG. 1 schematically illustrates an example ultrasound imaging system, including a touch screen keyboard (with an image display region) and a display monitor (with an image display region) that is a separate device relative to the touch screen keyboard.

FIG. 1 schematically illustrates an ultrasound (US) imaging system 102.

The ultrasound imaging system 102 includes a probe 104 with a one-dimensional (1D) or two-dimensional (2D) transducer array 106 with at least one transducer element 108. Suitable configurations include, but are not limited to, linear, curved (e.g., concave, convex, etc.), circular, etc., full populated or sparse, etc. The probe 104 further includes an interface 110. The interface 110 may include a connector (e.g., an electro-mechanical device for joining electrical circuits) and/or wireless transceiver.

The ultrasound imaging system 102 further includes a console 112. The console 112 includes an interface 114, which is complementary to the interface 110. With physical connectors, a communication device 116 such as a cable, a wire, an optical fiber, etc. electrically interfaces the interfaces 110 and 114. For example, the interface 110 may include a female connector and the communication device 116 may include a male connector, wherein the connectors physically engage and physically connect electrodes.

The console 112 further includes a transducer controller 118. The transducer controller 118 controls excitation of the at least one transducer element 108. The transducer controller 118 also controls detection of echoes with the at least one transducer element 108. The console 118 further includes an ultrasound processor 120 that processes detected echoes. Such processing may include generating an image, estimating flow velocity, and/or processing. A memory device 121 stores saved images.

The console 112 further includes an interface 124, which is a unidirectional interface in the illustrated embodiment. The console 112 utilizes the interface 124 to transmit information to an apparatus. For example, the console 112 can transmit images through the interface 124. In a variation, the interface 124 can be a bidirectional interface in that the interface 124 can receive information from the apparatus. Generally, the apparatus is a remote or separate apparatus (such as a display monitor) that is not part of the console 112.

The console 112 further includes an interface 126, which is a bidirectional interface. The console 112 utilizes the interface 126 to interact with an input/output (I/O) device, including transmitting information to and receiving information from the I/O device. In one instance, this includes transmitting one or more images to the I/O device and receiving control information from the I/O device. Generally, the I/O device can be part of the console 112 and includes a user interface with controls and a display that allows an operator to control the scanner 102 and view images.

The ultrasound imaging system 102 further includes a display monitor 122. The display monitor 122 can be a cathode ray tube (CRT), a liquid crystal display (LCD), a light emitting diode (LED), and/or other display monitor. The display monitor 122 includes a display region 124, which can visually present images and/or flow velocity information generated by the ultrasound processor 120. The display monitor 122 includes an interface 128, which is complementary to the interface 124. The interfaces 128 can include physical connectors and/or a wireless receiver.

In the illustrated embodiment, the display monitor 122 is affixed to a support 123. The support can be, for example, a stand that rests on a surface and holds the display monitor 122 in a generally upright position such that an observer can view images displayed thereby. In another instance, the support 123 can be a wall bracket that mounts to a wall, thereby indirectly mounting the display monitor 122 to a wall. Other supports are also contemplated herein. The support 123 may be configured to rotate, tilt, translate, and/or otherwise move, which selectively allows for spatially orienting the region 124.

The ultrasound imaging system 102 further includes a touch screen keyboard 130. The touch screen keyboard 130 includes at least controls 132, indicators 134, and an image display region 136. The touch screen keyboard 130 further includes an interface 138, which is complementary to the interface 126. The interfaces can include physical connectors and/or a wireless transceiver. In a configuration in which the touch screen keyboard 130 is part of the console 112, the interfaces 138 and 126 may alternatively be an internal connection such as a backplane, etc., and/or other connection.

In the illustrated embodiment, at least a sub-portion of the touch screen keyboard 130 includes a touch panel, in which predetermined active regions thereof evoke actions (e.g., through control signals) in response to being actuated by simple or multi-touch gestures of the screen with one or more fingers, a stylus, a glove, etc. The sub-portion may include sub-portions of one or more of the controls 132, the indicators 134, and the image display region 136. For example, sliding of two fingers together across the touch screen keyboard 130 over an image displayed in the image display region 136 may invoke generation of a zoom out control signal in connection with the displayed image.

An example of a suitable touch panel is described in application Ser. No. 13/748,653, filed on Jan. 24, 2013, and entitled "Ultrasound Imaging System," which is incorporated herein by reference in its entirety. As such the touch panel may include a resistive, capacitive, acoustic, infrared, optical, piezoelectric, and/or other panel. Furthermore, the touch panel may include a liquid crystal display (LCD), thin film transistor liquid crystal display (TFT LCD), organic light-emitting diode (OLED), and/or other display.

A display controller 140 at least controls the information visually presented on with display monitor 122. By way of example, in one non-limiting instance, actuation of one of the predetermined regions of the touch panel sub-regions of the touch screen keyboard 130 sends controls signals to the display controller 140, and the display controller 140 displays and/or controls display of an image displayed in the image display region 124 of the display monitor 122. As described in greater detail below, this may include presenting an initial image for display, removing a displayed image, replacing a displayed image with a different image, and/or other visualization based feature.

One or more of the components of FIG. 1 can be implemented via a computer processor executing computer readable instructions stored on computer readable storage medium (which exclude transitory medium). Additionally or alternatively, at least one of the computer readable instructions is carried by a signal, a carrier wave and/or other transitory medium.

Figure 2:
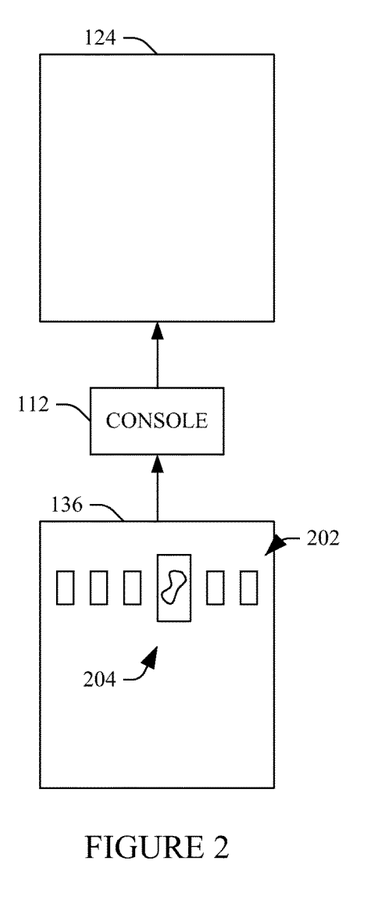
FIGS. 2 and 3 illustrate an example in which an image of interest is identified in the touch screen keyboard and displayed in the display monitor.
Figure 3:
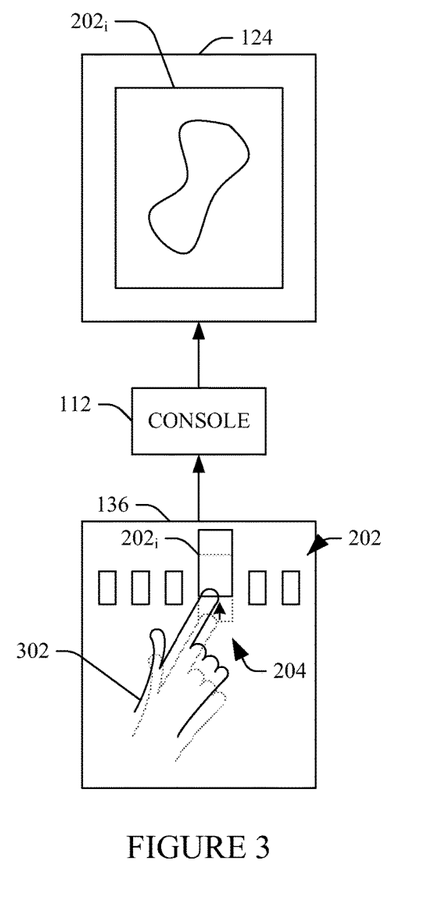

FIGS. 2 and 3 show an example in which one of a plurality images displayed in the image display region 136 of the touch screen keyboard 130 is identified and displayed in the image display region 124 of the display monitor 122.

Initially referring to FIG. 2, a plurality of images 202 are displayed, for example, as thumb nails, with an image of the plurality of images 202 at a position 204 displayed in a larger size relative to the other positions. The plurality of images 202 can be scrolled through by moving the plurality of images 202 one or more positions to the right or to the left. This can be achieved through swiping a suitable object (e.g., a stylus, a finger, etc.) across the plurality of images 202 in a direction of interest (left or right).

In another instance, this can be achieved by tapping or pressing an active region of the touch screen keyboard 130 in which each tap or press moves the plurality of images 202 one or more positions to the left or one or more positions to the right. In yet another example, this can be achieved by actuating an active region of the touch screen keyboard 130 that invokes automatic scrolling (left or right). Other approaches for scrolling through the images 202 are contemplated herein.

In a variation, more than one of the plurality of images 202 is displayed at a larger size relative to the other positions. In another variation, all of the plurality of images 202 is displayed at a same size. In another variation, the plurality of images 202 is displayed in a vertical manner, a diagonal manner, or otherwise instead of a horizontal manner, as shown in FIG. 2. Six images are shown in the illustrated example. It is to be understood that more or less images can be displayed.

Turning to FIG. 3, an object 302 (a finger in this example) identifies an image $202_i$ of the plurality of images 202 for display in the image display region 124 of the display monitor 122. In the illustrated embodiment, this is achieved by dragging the image $202_i$ in a direction of the image display region 124 of the display monitor 122, e.g., from a border region of the image $202_i$. Although the bottom border is shown, the image $202_i$ can be dragged from a side or top border. Other approaches are also contemplated herein.

The particular image displayed in the image display region 124 of the display monitor 122 can be changed by dragging another image to the image display region 124 of the display monitor 122. In a variation, the displayed image 202i can be removed by dragging the image in the touch screen keyboard in the opposite direction, or away from the image display region 124. Similar to the initial display, the object 302 drags the image from a border region of the image 202.

Figure 4:
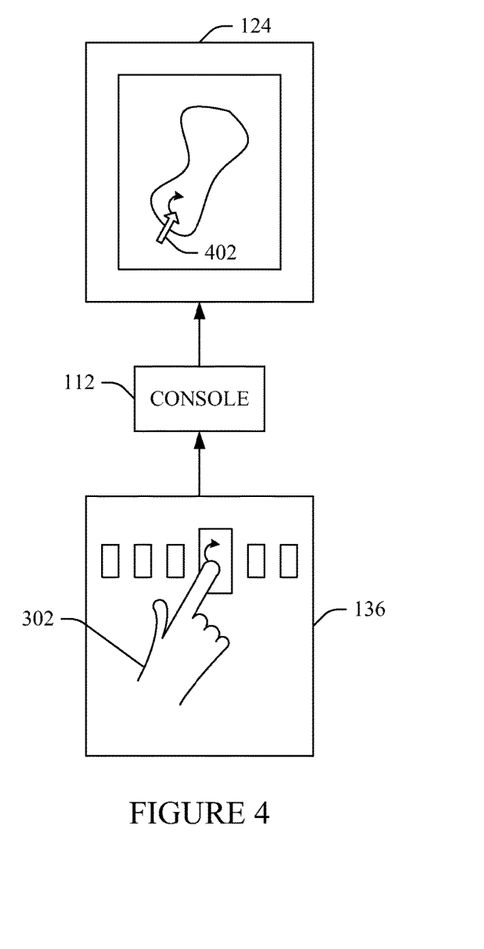
FIG. 4 illustrates an example in which a pointer is created and manipulated in the display monitor through interaction with the touch screen keyboard.

In FIG. 4, a pointer 402 is created for the image display region 124 of the display monitor 122 by pressing with the object 302 within the border of the image displayed in the image display region 136 of the touch screen keyboard 130. The pointer 402 can be moved, for example, to point to a particular part of the image, by moving the object 302 over the image display region 136 of the touch screen keyboard 130 while maintaining depression of the object within the border.

Other visualization features can be activated using a similar approach. For example, to zoom in or zoom out of the image displayed in the image display region 124 of the display monitor 122, the user, respectively, places two fingers on the touch screen keyboard 130 and slides the fingers within the border across the touch screen keyboard 130 away from each other or slides the fingers across the touch screen keyboard 130 towards each other.

For rotating the image, the user places two fingers on the touch screen keyboard 130 and slides their fingers through an arc in the direction of rotation of interest. For panning the image, the user places a finger on the touch screen keyboard 130 and slides their finger within the border along a line in the direction of interest. Other image manipulation features are also contemplated herein. Furthermore, two or more of these features can be concurrently activated.

Figure 5:
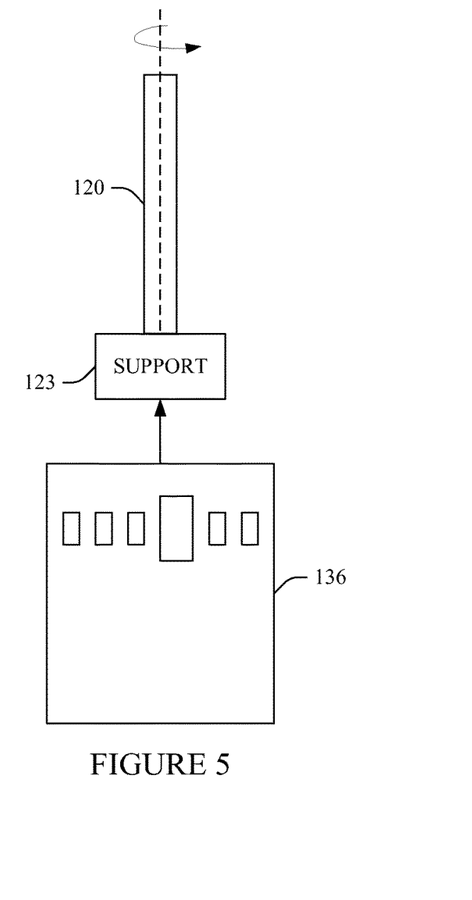
FIG. 5 illustrates an example in which the display monitor is rotated with respect to the touch screen keyboard.

As described herein, the display monitor 122 is affixed to the support 123 and can rotate, tilt, translate, and/or otherwise move with respect thereto. In FIG. 5, the display monitor 122 is rotated 90 degrees. Such motion is well-suited for turning the display monitor 122 so that the image displayed via the display monitor 122 is viewable to one or more observers, other than or including the person operating the ultrasound imaging system 102, who can additionally or alternatively see and manipulate the image via the image display region 136 of the touch screen keyboard 130.

Figure 6:
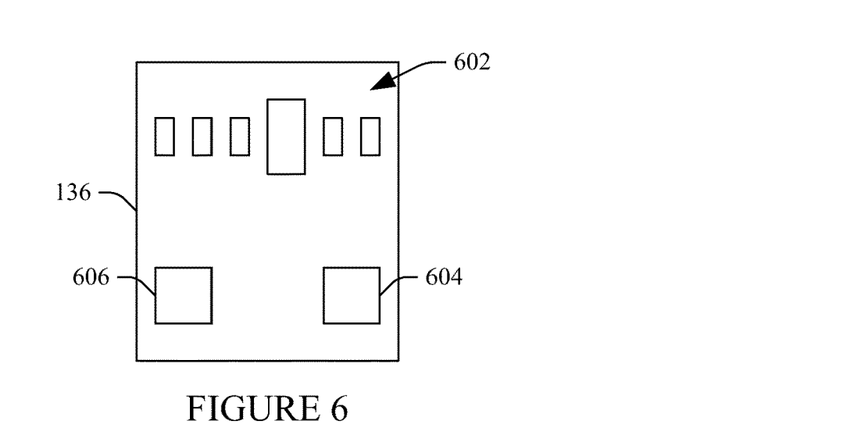
FIG. 6 illustrates an example in which the touch screen keyboard includes an image save active region and an image delete active region.

In FIG. 6, a plurality of images 602 are displayed, e.g., as thumb nails and can be scrolled through by moving the plurality of images 602 to the right or one position to the left by swiping the object (not shown for clarity) across the plurality of images 602 in a direction of interest, as described herein and/or otherwise. In this example, the touch screen keyboard 130 also includes an image save active region 604 and an image delete active region 606.

Figure 7:
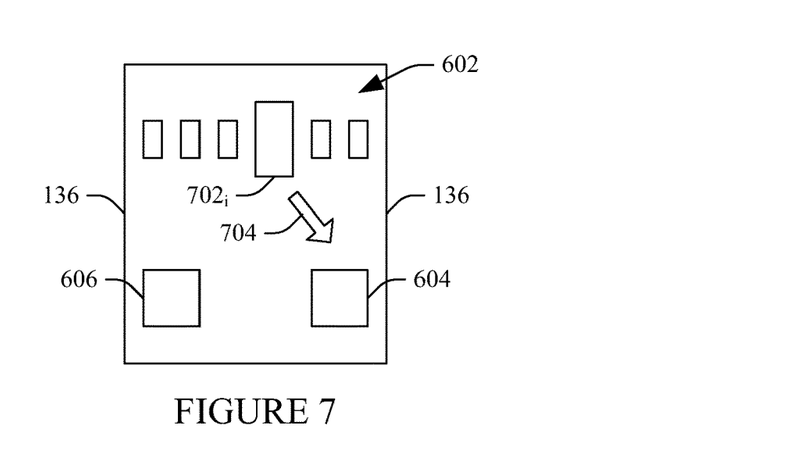
FIG. 7 illustrates an example of saving an image displayed in the touch screen keyboard using the image save active region.

With respect to FIGS. 6 and 7, the object (not shown for clarity) is used to identify an image $702_i$ to be saved, similar to identifying an image for display. In the illustrated embodiment, this is achieved by dragging, via swiping (indicated by arrow 704), the image $702_i$ from its border to the image save active region 604 of the touch screen keyboard 130 and then removing the object from the touch screen keyboard 130. Other approaches are also contemplated herein.

Figure 8:
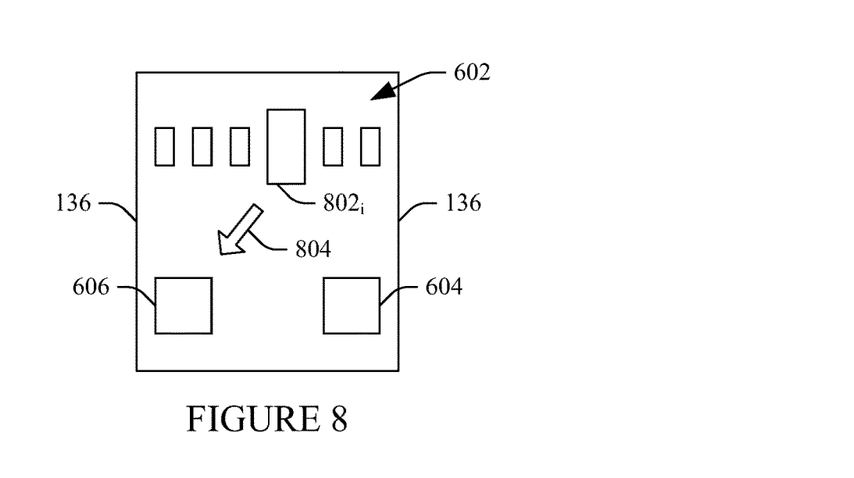
FIG. 8 illustrates an example of deleting an image displayed in the touch screen keyboard using the image delete active region.

With respect to FIGS. 6 and 8, the object (not shown for clarity) is used to identify an image $802_i$; to be saved, similar to identifying an image for display and/or saving. In the illustrated embodiment, this is achieved by dragging, via swiping (indicated by arrow 804), the image $802_i$; from its border to the image delete active region 606 of the touch screen keyboard 130 and then removing the object from the touch screen keyboard 130. Other approaches are also contemplated herein.

Figure 9:
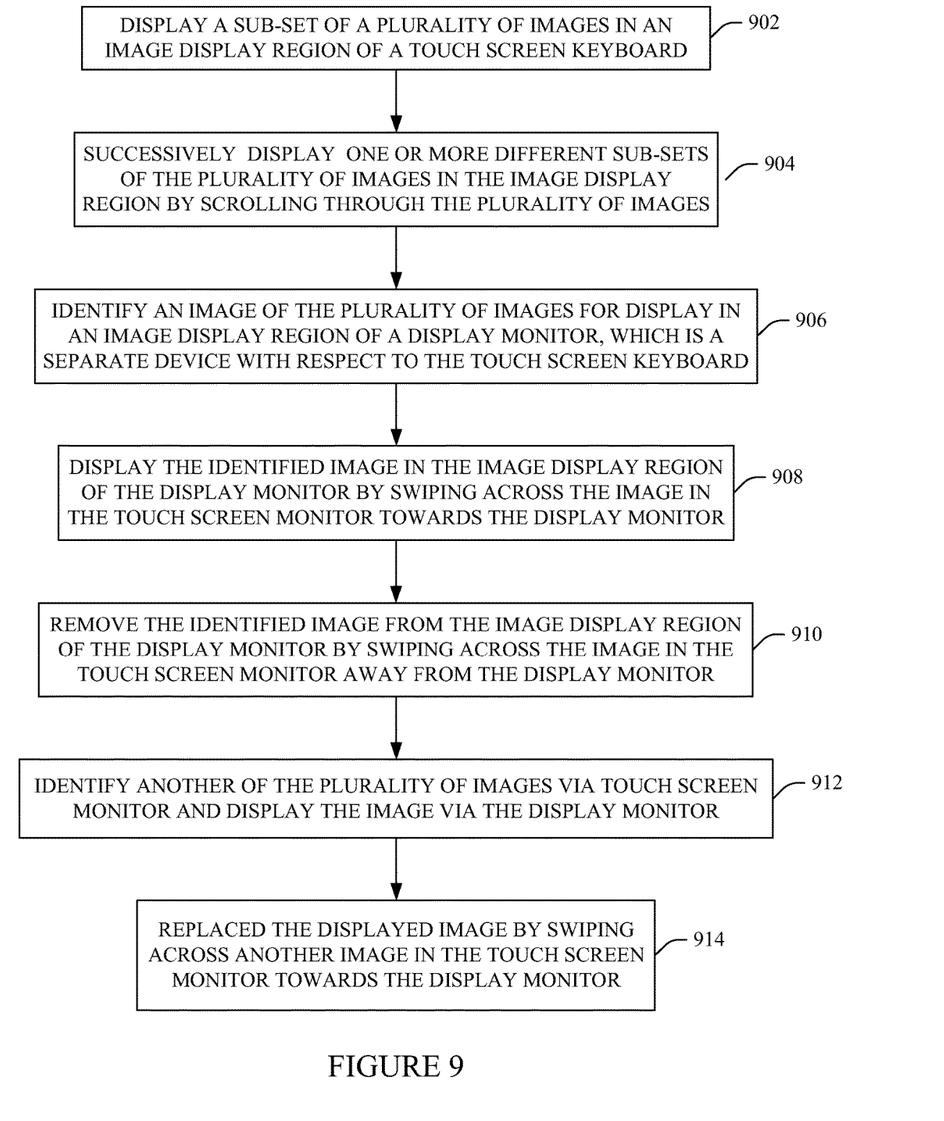
FIG. 9 illustrates a method for displaying an image in an image display region of a display monitor via identifying the image in an image display region of a touch screen keyboard.
Figure 10:
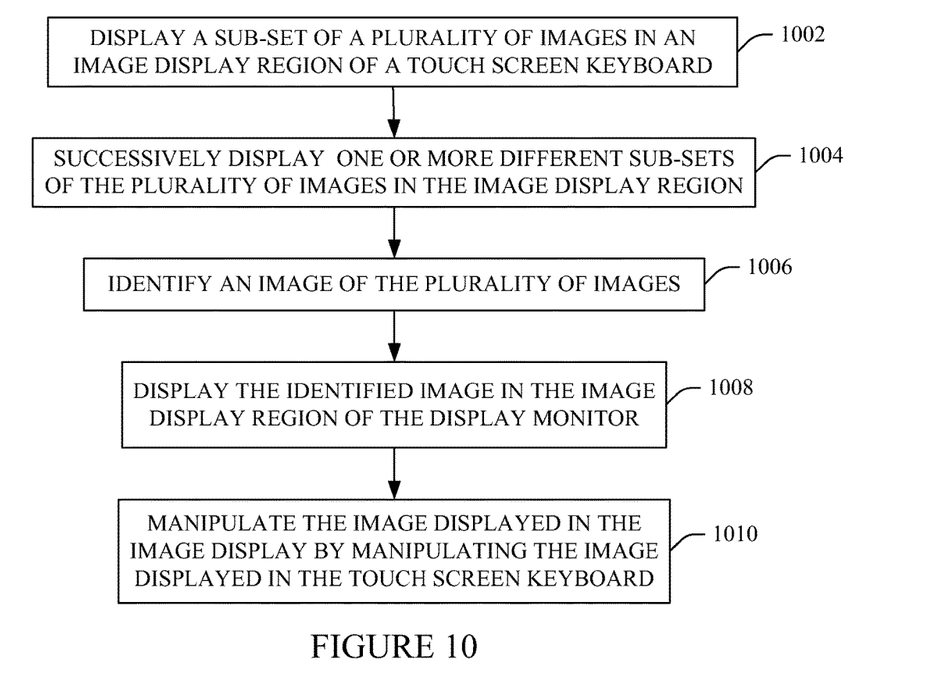
FIG. 10 illustrates a method for manipulating an image displayed in an image display region of a display monitor via an image display region of a touch screen keyboard.
Figure 11:
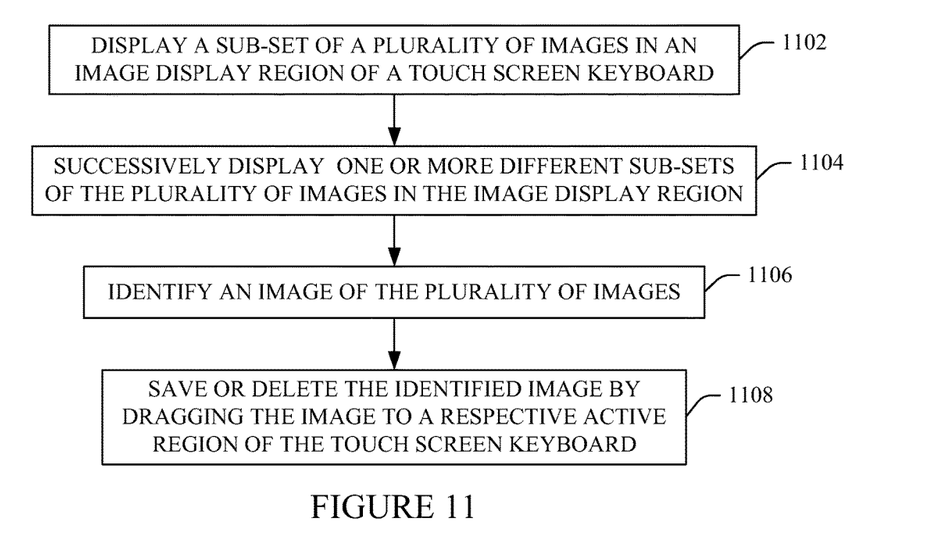
FIG. 11 illustrates a method for saving or deleting an image displayed in an image display region of a touch screen keyboard.

FIGS. 9, 10 and 11 illustrate example methods in accordance with the embodiments described herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

FIG. 9 illustrates a method for displaying an image in an image display region of a display monitor via identifying the image in an image display region of a touch screen keyboard, which is a separate device with respect to the display monitor.

At 902, a sub-set of a plurality of images is displayed in an image display region of a touch screen keyboard of an ultrasound imaging system.

At 904, optionally, one or more different sub-sets of the plurality of images are successively displayed by scrolling through the plurality of images, as described herein and/or otherwise.

At 906, an image of interest of the plurality of images is identified for display in an image display region of a display monitor, which is a separate device, relative to the touch screen keyboard.

At 908, the identified image of interest is displayed in the image display region of the display monitor, as described herein, for example, by swiping across the image displayed on the touch screen keyboard in a direction toward the display monitor.

At 910, optionally, the identified image of interest is removed from image display region of the display monitor, as described herein, for example, by swiping across the image displayed on the touch screen keyboard in a direction away from the display monitor.

At 912, optionally, another image is identified via the touch screen keyboard and displayed in the image display region of the display monitor.

At 914, optionally, the displayed image of interest is replace with another image of interest, as described herein, for example, by swiping across the image displayed on the touch screen keyboard in the direction of the display monitor.

FIG. 10 illustrates a method for manipulating an image displayed in an image display region of a display monitor via an image display region of a touch screen keyboard, which is a separate device with respect to the display monitor.

At 1002, a sub-set of a plurality of images is displayed in an image display region of a touch screen keyboard of an ultrasound imaging system.

At 1004, optionally, one or more different sub-sets of the plurality of images are successively displayed by scrolling through the plurality of images.

At 1006, an image of interest of the plurality of images is identified for display in an image display region of a display monitor, which is a separate device with respect to the touch screen keyboard.

At 1008, the identified image of interest is displayed in the image display region of the display monitor, as described herein.

At 1010, the identified image of interest is manipulated (e.g., rotated, panned, zoomed, etc.) in the image display region of the display monitor, as described herein, for example, by manipulating the corresponding image displayed on the touch screen keyboard.

FIG. 11 illustrates a method for saving or deleting an image displayed in an image display region of a touch screen keyboard.

At 1102, a sub-set of a plurality of images is displayed in an image display region of a touch screen keyboard of an ultrasound imaging system.

At 1104, optionally, one or more different sub-sets of the plurality of images are successively displayed by scrolling through the plurality of images.

At 1106, an image of interest of the plurality of images is identified. At 1108, the identified image of interest is saved or deleted by swiping across the image displayed on the touch screen keyboard in a direction towards a save active region of the touch screen keyboard or a delete active region of the touch screen keyboard.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    displaying a set of two or more images of a plurality of images in a row displayed on an image display region of a touch screen keyboard of an ultrasound imaging system, wherein each displayed image has a visible boundary;
    displaying a different set of two or more images of the plurality of images in the row on the image display region of the touch screen keyboard by scrolling through the plurality of images;
    moving an object from the boundary of one of the plurality of images displayed with the touch screen keyboard in a first direction, which generates a first signal
    receiving the first signal from the touch screen keyboard, wherein the first signal indicates the one of the plurality of images is to be displayed with a display monitor of the ultrasound imaging system, wherein the touch screen keyboard and the display monitor are separate devices; and
    displaying the one of the plurality of images with the display monitor in response to the first signal.

2. The method of claim 1, further comprising:
    receiving a second signal from the touch screen keyboard indicating removal of the one of the plurality of images from the display monitor; and
    removing the one of the plurality of images from the display monitor.

3. The method of claim 2, further comprising:
    moving the object from the boundary of the one of the plurality of images displayed with the touch screen keyboard in a second different direction, thereby generating the second signal.

4. The method of claim 1, further comprising:
    receiving a second signal from the touch screen keyboard indicating replacing the one of the plurality of images displayed with the display monitor with another one of the plurality of images; and
    replacing the one of the plurality of images with the other one of the plurality of images in the display monitor.

5. The method of claim 4, further comprising:
    moving the object from the boundary of the another one of the plurality of images displayed with the touch screen keyboard in the first direction, thereby generating the second signal.

6. The method of claim 1, further comprising:
    receiving a second signal from the touch screen keyboard indicating rotating the one of the plurality of images displayed with the display monitor; and
    rotating the one of the plurality of images based on the second signal.

7. The method of claim 6, further comprising:
    rotating the object over the one of the plurality of images displayed with the touch screen keyboard in a rotation direction of interest, thereby generating the second signal.

8. The method of claim 1, further comprising:
    receiving a second signal from the touch screen keyboard indicating a zoom factor for the one of the plurality of images displayed with the display monitor; and
    zooming the one of the plurality of images based on the second signal.

9. The method of claim 8, further comprising:
    moving the object over the one of the plurality of images displayed with the touch screen keyboard to identify a zoom factor of interest, thereby generating the second signal.

10. The method of claim 1, further comprising:
    receiving a second signal from the touch screen keyboard indicating panning the one of the plurality of images displayed with the display monitor; and
    panning the one of the plurality of images based on the second signal.

11. The method of claim 10, further comprising:
    moving the object over the one of the plurality of images displayed with the touch screen keyboard to identify a pan direction of interest, thereby generating the second signal.

12. The method of claim 1, further comprising:
    receiving a second signal from the touch screen keyboard indicating a location of a moveable pointer for the one of the plurality of images displayed with the display monitor; and placing the moveable pointer at the location based on the second signal.

13. The method of claim 12, further comprising:
depressing, with the object, within a border of the one of the plurality of images displayed with the touch screen keyboard to identify the location, thereby generating the second signal.

14. The method of claim 13, further comprising:
translating, with the object, within the border, to identify a next location, thereby updating the second signal.

15. The method of claim 1, further comprising:
displaying the set of two or more images of the plurality of images as thumb nails in the row displayed on the image display region of the touch screen keyboard of the ultrasound imaging system.

16. The method of claim 15, further comprising:
displaying one of the displayed two or more images with a first size; and
displaying another one of the displayed two or more images with a second different size.

17. The method of claim 1, wherein the set of two or more images is at a first position in the row, and further comprising:
scrolling through the plurality of images by moving the set of two or more images one or more positions to the right or to the left of the current position.

18. The method of claim 17, further comprising:
moving the set of two or more images by swiping the object across the plurality of images.

19. The method of claim 17, further comprising:
moving the set of two or more images by tapping an active region of the touch screen keyboard in which each tap moves the plurality of images one or more positions to the left or one or more positions to the right of the current position.

20. The method of claim 17, further comprising:
moving the set of two or more images by pressing an active region of the touch screen keyboard in which each press moves the plurality of images one or more positions to the left or one or more positions to the right of the current position.

21. The method of claim 17, further comprising:
moving the set of two or more images by actuating an active region of the touch screen keyboard that invokes automatic scrolling.

22. The method of claim 1, further comprising:
moving the object from the boundary of the one of the plurality of images displayed with the touch screen keyboard in the first direction by dragging the one of the plurality of images in a direction of an image display region of the display monitor.

23. The method of claim 1, further comprising:
saving the one of the plurality of images by moving it with the object to a save region of the touch screen keyboard.

24. The method of claim 1, further comprising:
deleting the one of the plurality of images by moving it with the object to a delete region of the touch screen keyboard.

25. The method of claim 1, wherein the display monitor is affixed to a support and is configured to rotate relative to the support, and further comprising:
rotating the display monitor relative to the support.

* * * * *